(12) United States Patent
Wells

(10) Patent No.: US 8,267,897 B2
(45) Date of Patent: Sep. 18, 2012

(54) CENTER TWIST HEMOSTATIC VALVE

(75) Inventor: Dax B. Wells, Provo, UT (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 12/683,174

(22) Filed: Jan. 6, 2010

(65) Prior Publication Data

US 2011/0166527 A1 Jul. 7, 2011

(51) Int. Cl.
*A61M 5/178* (2006.01)

(52) U.S. Cl. .................................................. 604/167.05

(58) Field of Classification Search ............. 604/167.05, 604/248, 256; 251/210, 211, 212, 335.2
See application file for complete search history.

(56) References Cited

U.S. PATENT DOCUMENTS

| | | | |
|---|---|---|---|
| 2,275,654 A * | 3/1942 | Ravenscroft et al. ............ | 53/451 |
| 2,844,351 A * | 7/1958 | Smith ................................ | 251/4 |
| 3,329,390 A * | 7/1967 | Hulsey ............................... | 251/4 |
| 4,307,868 A | 12/1981 | Morin | |
| 4,540,411 A | 9/1985 | Bodicky | |
| 5,005,113 A | 4/1991 | Ohtuka et al. | |
| 5,158,553 A * | 10/1992 | Berry et al. ................... | 604/248 |
| 5,197,955 A | 3/1993 | Stephens et al. | |
| 5,211,370 A | 5/1993 | Powers | |
| 5,256,150 A | 10/1993 | Quiachon et al. | |
| 5,324,271 A | 6/1994 | Abiuso et al. | |
| 5,350,363 A | 9/1994 | Goode et al. | |
| 5,484,418 A * | 1/1996 | Quiachon et al. ......... | 604/167.03 |
| 5,779,681 A | 7/1998 | Bonn | |
| 6,086,570 A | 7/2000 | Aboul-Hosn et al. | |
| 6,276,661 B1 | 8/2001 | Laird | |
| 6,416,499 B2 | 7/2002 | Paul, Jr. | |
| 6,610,031 B1 | 8/2003 | Chin | |
| 7,172,580 B2 * | 2/2007 | Hruska et al. .................. | 604/248 |
| 7,470,261 B2 * | 12/2008 | Lynn .............................. | 604/256 |
| 7,713,242 B2 * | 5/2010 | Streifinger et al. ....... | 604/167.04 |
| 7,731,694 B2 * | 6/2010 | Becker et al. ............. | 604/167.06 |
| 2005/0171479 A1 * | 8/2005 | Hruska et al. ............. | 604/167.06 |
| 2007/0112409 A1 | 5/2007 | Wu et al. | |
| 2008/0157017 A1 * | 7/2008 | Macatangay et al. ......... | 251/314 |
| 2008/0208175 A1 * | 8/2008 | Beckman et al. .................. | 606/1 |
| 2010/0063362 A1 * | 3/2010 | Bonadio et al. ............... | 600/203 |

FOREIGN PATENT DOCUMENTS

| | | |
|---|---|---|
| EP | 0550069 | 7/1993 |
| EP | 0564578 | 10/1993 |
| WO | 01/70308 | 9/2001 |
| WO | 2005/058409 | 6/2005 |

* cited by examiner

*Primary Examiner* — Nicholas Lucchesi
*Assistant Examiner* — Diva K Chander
(74) *Attorney, Agent, or Firm* — Gilbert R. Gabo

(57) ABSTRACT

The invention comprises a hemostatic valve apparatus used in medical procedures that provides a valve that is always sealed. The valve apparatus incorporates a double twist and a rotation member placed between the ends of the valve. Because the valve is never fully opened, either no fluids or an insignificant amount of fluids will flow when used in surgical or interventional procedures. The invention also comprises a valve conduit with first and second fixed ends and a rotatable member positioned between the first and second ends.

54 Claims, 6 Drawing Sheets

CENTER TWIST HEMOSTATIC VALVE

FIELD OF THE INVENTION

The invention relates to a valve for use in medical applications, more preferably a hemostasis valve apparatus used in medical procedures.

BACKGROUND

Hemostatic valves are used in a wide variety of minimally invasive and conventional surgical procedures. For example, laparoscopic and arthroscopic surgical procedures are often performed through trocar or introducer assemblies which include hemostatic valves. After a trocar or introducer sheath is inserted to provide access to a body target site, surgical instruments, tools, guidewires, implantable devices or diagnostic instruments are inserted into and withdrawn from a hemostatic sealing valve located at a proximal end of the trocar or introducer. The hemostatic valve generally prevents fluid from inadvertently leaving or entering the body target site through the trocar or introducer. As advanced surgical procedures have emerged, hemostatic valves have faced more stringent demands. For example, a wider range of device profiles and a greater number of devices are often passed through a single hemostatic valve.

Current hemostatic valves generally fall into two basic categories: passive and active. To form the desired fluid tight seal, a passive valve generally relies on a resilient sealing body being deformed by the device as it is inserted through the valve. An active valve includes a means to move a sealing body into contact with the traversing device.

A wide variety of active and passive hemostatic valves have been proposed. While these structures have met with varying degrees of success and acceptance, they generally have suffered from common disadvantages. For example sealing bodies (whether passive or active) which seal effectively over a wide range of device cross-sectional profiles tend to impose excess friction on at least some sizes of traversing devices. Active devices which seal effectively over a wide range of device cross-sectional profiles have the disadvantage of requiring extended actuation travel (i.e. thumb or finger motion) along with excessive time to fully open and close the sealing device.

It would be desirable to provide an improved hemostatic valve for use in endovascular, laparoscopic and other surgical procedures. Such a valve should preferably seal over a wide range of device sizes, cross-sectional profiles and lengths without imposing excess friction onto the device. In addition, such a valve should preferably be actuated with a finger or thumb motion and be able to be fully opened or closed in a minimal amount of time and without requiring extended actuation travel.

SUMMARY OF THE INVENTION

Accordingly, the invention comprises a hemostatic valve apparatus used in medical procedures that substantially obviates one or more of the problems due to limitations and disadvantages of the related art.

The instant invention comprises a hemostatic valve comprising, a valve conduit with first and second regions, said regions each having an open and closed configuration, wherein said valve conduit is open in one region and closed in the other region; and a rotation member attached to said conduit, wherein when said rotation member is actuated, said actuation alternates each region between open and closed configurations. In one embodiment, said valve conduit is never fully opened. In another embodiment, said rotatable member is directly attached to the valve conduit. In another embodiment, wherein said valve conduit comprises a material selected from the group consisting of expanded polytetrafluoroethelene (ePTFE), silks, polyester weaves and porous filled materials. In another embodiment, said valve further comprises at least one additional sealing mechanism. In another embodiment, said at least one additional sealing mechanism is selected from the group consisting of an elastic diaphragm, a cap, a twistable conduit, brushes, and an inflatable valve or a combination thereof.

The invention also comprises hemostatic valve comprising, a twistable valve conduit with first and second fixed ends and a rotatable member positioned between the first and second ends. In one embodiment, said valve is never fully opened. In another embodiment, said rotatable member is directly attached to the valve conduit. In another embodiment, said hemostatic valve further comprises a latch or means of holding said rotatable member in place when said rotatable member is actuated. In another embodiment, said twistable valve conduit comprises a material selected from the group consisting of expanded polytetrafluoroethelene (ePTFE), silks, polyester weaves and porous filled materials. In another embodiment, said twistable valve conduit comprises two or more different materials having different mechanical properties such as durometers or degrees of elasticity. In another embodiment, said hemostatic valve further comprises at least one additional sealing mechanism. In another embodiment, said at least one additional sealing mechanism is selected from the group consisting of an elastic diaphragm, a cap, a twistable conduit, brushes, and an inflatable valve or a combination thereof.

The invention also comprises a medical apparatus, comprising, a housing, a sheath, and a valve, wherein said valve comprises a twistable valve conduit with first and second fixed ends and a rotatable member positioned between the first and second ends. In one embodiment, said valve is never fully opened. In another embodiment, said medical apparatus prevents the loss of bodily fluids. In another embodiment, said medical apparatus is a vascular introducer sheath.

The invention also comprises a hemostatic valve comprising, a twistable valve conduit with first and second fixed ends and a rotatable member positioned between the first and second ends and wherein said valve conduit is open at both ends. In one embodiment, when the rotatable member is actuated, the valve conduit will twist the valve conduit thus closing the valve. In another embodiment, said valve conduit will twist shut on both sides of the rotation member.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and incorporated in and constitute a part of this specification, illustrate embodiments of the invention and together with the descrip

DETAILED DESCRIPTION OF THE ILLUSTRATED EMBODIMENTS

The invention relates to a valve apparatus for use in medical applications, more preferably a hemostatic valve apparatus used in medical procedures. The medical procedures comprise, but not limited to, laparoscopic, endoscopic, and other medical procedures.

Reference will now be made in detail to an embodiment of the present invention, examples of which are illustrated in the accompanying drawings.

Figure 1A:
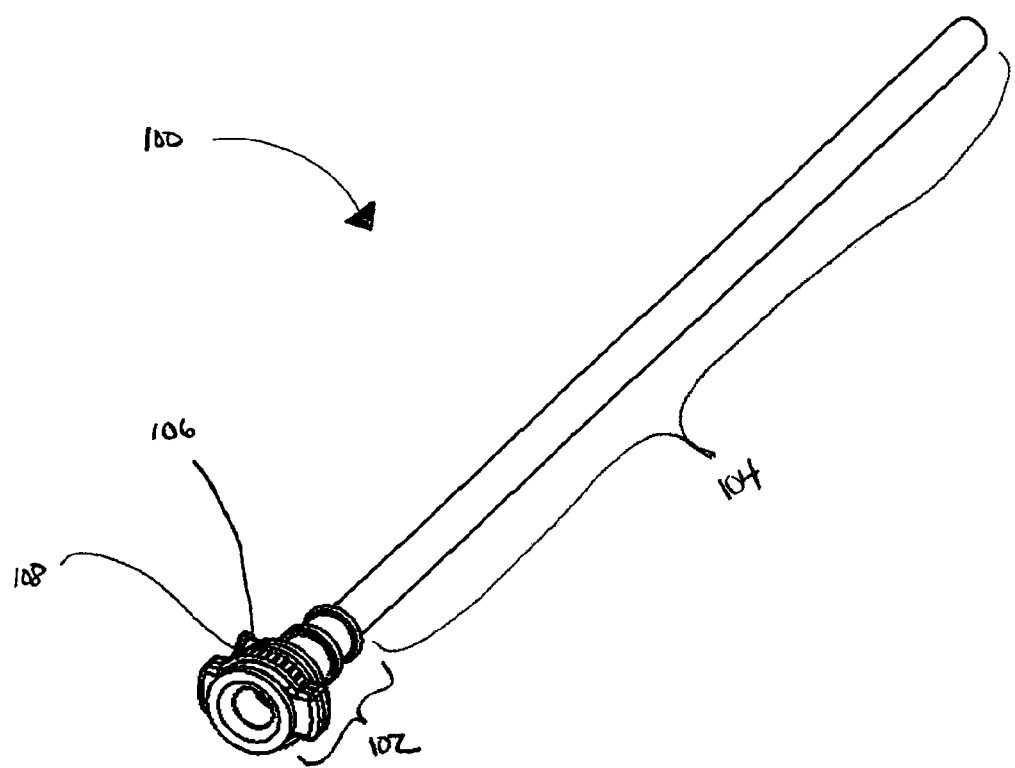
- FIG. 1A depicts a fully assembled introducer sheath (isometric view) according to an embodiment of the invention.
Figure 1B:
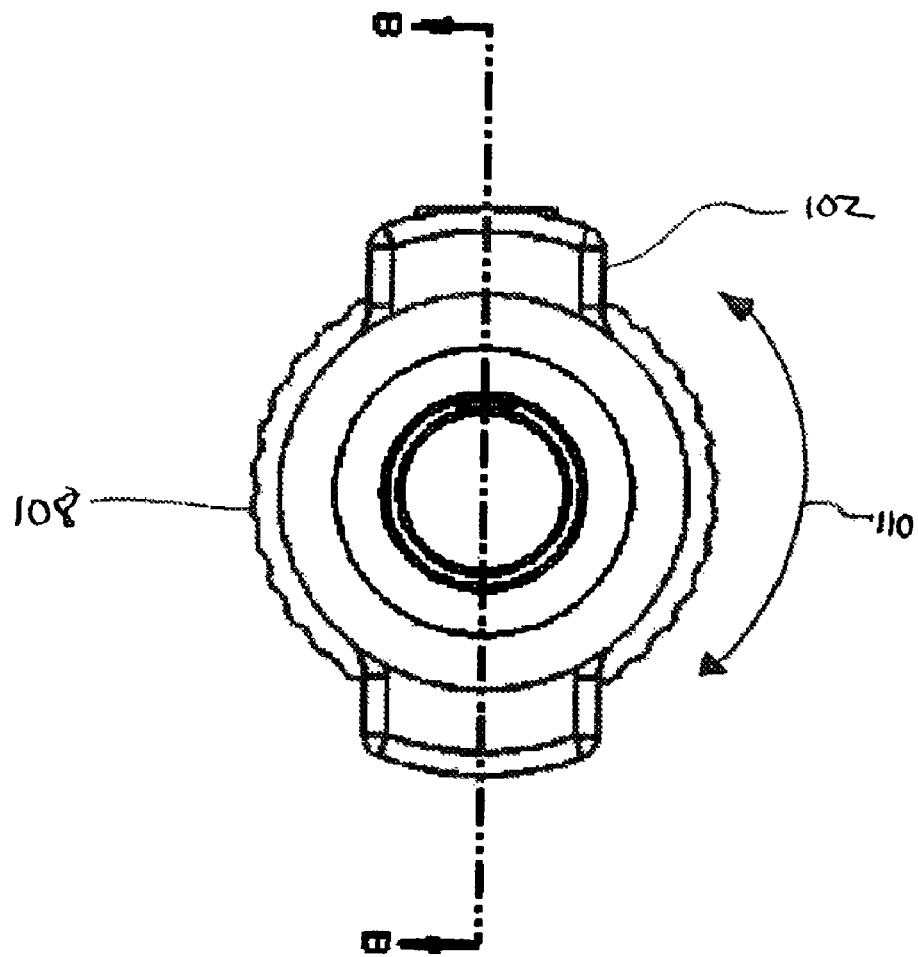
FIG. 1B is an end view of the introducer sheath from the housing.

Referring to FIG. 1A, an introducer sheath according to an embodiment of the invention is generally depicted as reference number 100. The apparatus 100 includes a housing 102 and a sheath 104 connected to housing 102 (see also FIG. 3). Housing 102 comprises a valve (i.e. a hemostatic valve) which comprises a valve conduit (see FIG. 3 302) a rotation member 108 that partially extends outside of the housing (see FIG. 1B). Rotation member 108 can be actuated in the direction according the arrow 110 (FIG. 1B). An ergonomic feature (as shown in FIGS. 1A and B) can help user grip rotation member 108 for easy turning. This feature can also be used to keep rotation member in place once it is turned (see below for further a description). In one embodiment, said actuator can be turned using operator's hand. In another embodiment, said actuator can be turned using only a thumb or a thumb and forefinger.

Sheath 104 may be manufactured of either fluorinated ethylene propylene (FEP) or extruded high density polyethylene or any other material with suitable biocompatible and mechanical properties. One of skill in the art can readily appreciate that there are a wide variety of potential materials that can be used to facilitate the present invention. Sheath 104 may be of any size diameter. In one embodiment, sheath 104 is from about 12 to about 26 Fr. The proximal most end of the sheath 104 may comprise a flange that will keep sheath 104 from sliding longitudinally within housing 102 or said sheath can be bonded to the housing. Sheath 104 may be attached to housing 102 in a variety of ways. In one embodiment, sheath 104 may be attached to the housing 102 by using adhesives such as polyurethane adhesives, quick setting cyanoacrylate adhesives or ultraviolet cure adhesives. In another embodiment, sheath 104 is attached to housing 102 by ultrasonic welding, interference fit, thermal bond, insert molding or a combination thereof. One of skill in the art can readily appreciate that there are a wide variety of potential means for attaching sheath 104 to housing 102. Said attachment of sheath 104 to housing 102 will create a leak proof attachment. For the purposes of this invention, the terms "leak proof attachment" and "leak proof seal" means that either no fluids or an insignificant amount of fluids will leak from said attachment or seal when used in surgical or interventional procedures. In another embodiment, housing 102 can be comprised of several sections that are joined together to form housing 102 and may enclose a number of components, as described below. In another embodiment, said housing sections are joined together by adhesives, any method described above or method known in the art.

Figure 2A:
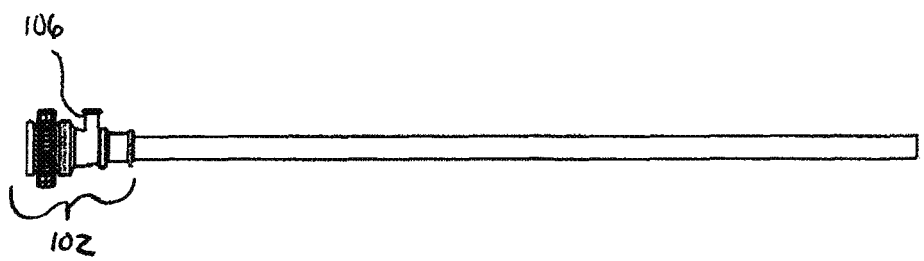
FIGS. 2 A and B depict a fully assemble introducer sheath with (A) and without (B) a flush port.
Figure 2B:
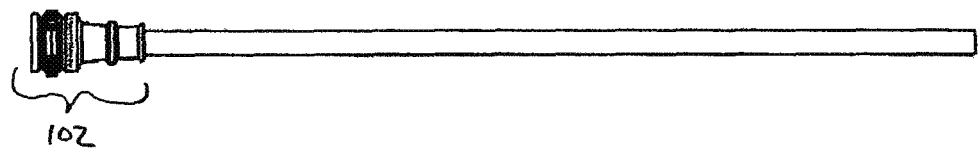

Said housing 102 can be constructed out of polymethyl methacrylate (PMMA or Acrylic), polystyrene (PS), acrylonitrile butadiene styrene (ABS), polyvinyl chloride (PVC), modified polyethylene terephthalate glycol (PETG), cellulose acetate butyrate (CAB), polyethylene (PE), high density polyethylene (HDPE), low density polyethylene (LDPE or LLDPE), polypropylene (PP), polycarbonate (PC), modified polyphenylene oxide (Mod PPO), polyphenelyne ether (PPE), thermoplastic polyurethane (TPU), polyamide (PA or Nylon), polyoxymethylene (POM or Acetal), polyethylene terephthalate (PET, Thermoplastic Polyester), polybutylene terephthalate (PBT, thermoplastic polyester), ultra high molecular weight polyethylene (UHMW-PE), fluorinated ethylene propylene (FEP), or any other medical grade polymer commonly known in the art. In one embodiment, said housing can include a flush-port 106. The function and use of flushing port 106 and fitting are commonly known in the art. FIGS. 2A and 2B depict embodiments of housing 102 with (102A) and without (102B) a flush port. In either embodiment, such an attachment should be a leak proof attachment. In another embodiment, housing 102 can be comprised of several sections that are joined together to form housing 102 and may enclose a number of components, as described below. In another embodiment, said housing sections are joined together by adhesives, any method described above, or a method known in the art.

Figure 3A:
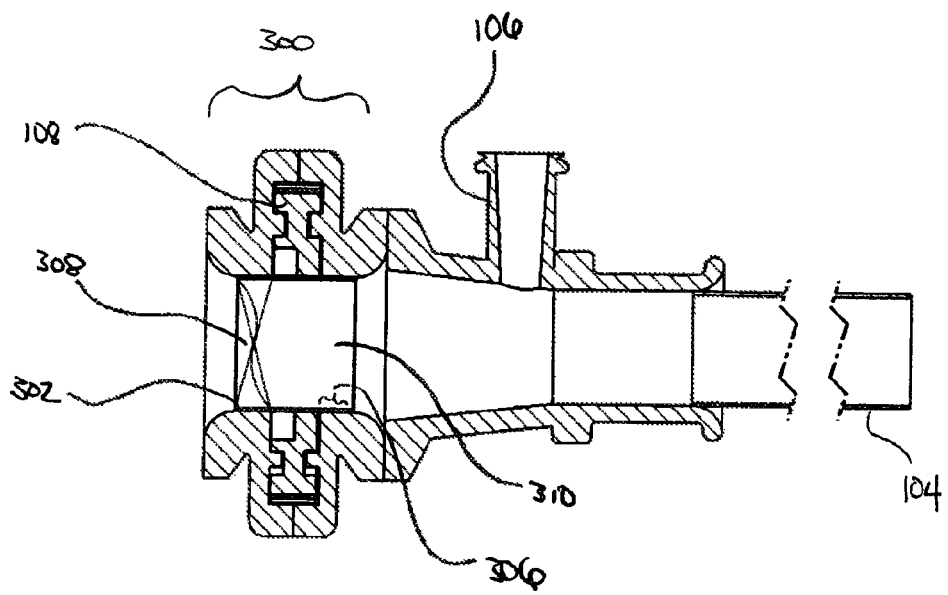
FIGS. 3 A, B and C depict a cross section of an introducer sheath.
Figure 3B:
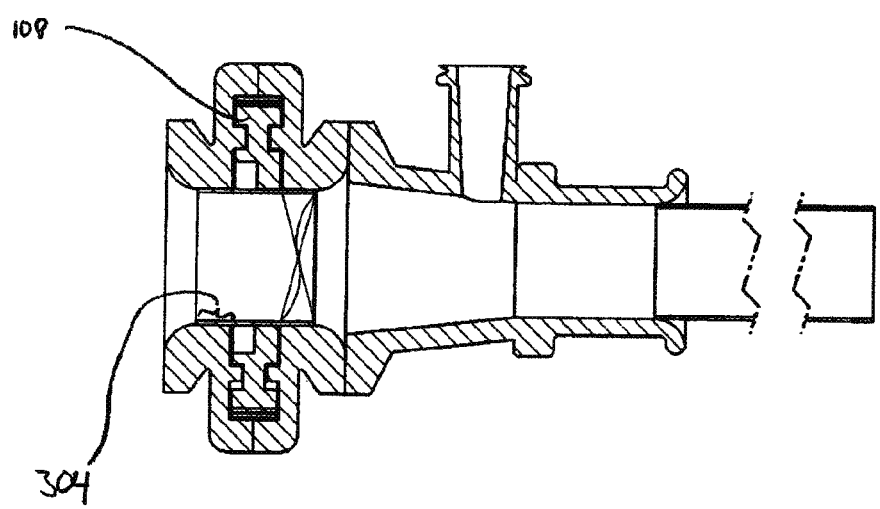

Now, referring to FIG. 3, which comprises a cross section of housing 102 in the plane B-B as depicted in FIG. 1B. Said housing comprises the valve of the invention. One embodiment of the invention comprises valve 300 comprising, a valve conduit 302 with first 304 and second 306 regions, said regions each having an closed 308 and open 310 configuration, wherein said valve conduit 302 is open 310 in one region and closed 308 in the other region; and a rotation member 108 attached to said conduit, wherein when said rotation member 108 is actuated in any direction in accordance to the arrow 110 in FIG. 1B, said actuation alternates each region between closed 308 and open 310 configurations, as depicted in FIGS. 3A and 3B. In one embodiment, said valve conduit is never fully opened. Because the valve is never fully opened, either no fluids or an insignificant amount of fluids will flow (i.e. leak) when used in surgical or interventional procedures. In another embodiment, said rotatable member 108 is directly attached to valve conduit 302. Said rotatable member can be attached to the valve conduit by adhesives (as described below) or other methods known in the art. In another embodiment, said rotatable member can be indirectly attached to the valve conduit. In another embodiment, said rotation member is attached in between said first and second regions (i.e. between the ends) of said valve conduit. In another embodiment, said rotation member is attached in the center of said valve conduit. In another embodiment, said rotation member is attached off center (in either direction) of said valve conduit.

In another embodiment, said valve of the invention is a component of a vascular introducer sheath. An example of an introducer sheath is shown in FIG. 1A. In another embodiment, at least one region of said valve conduit collapses around at least one medical device inserted into said conduit when said rotation member is actuated. In one embodiment, said medical device is selected from the group consisting of catheters, sheaths, and guidewires.

Figure 3C:
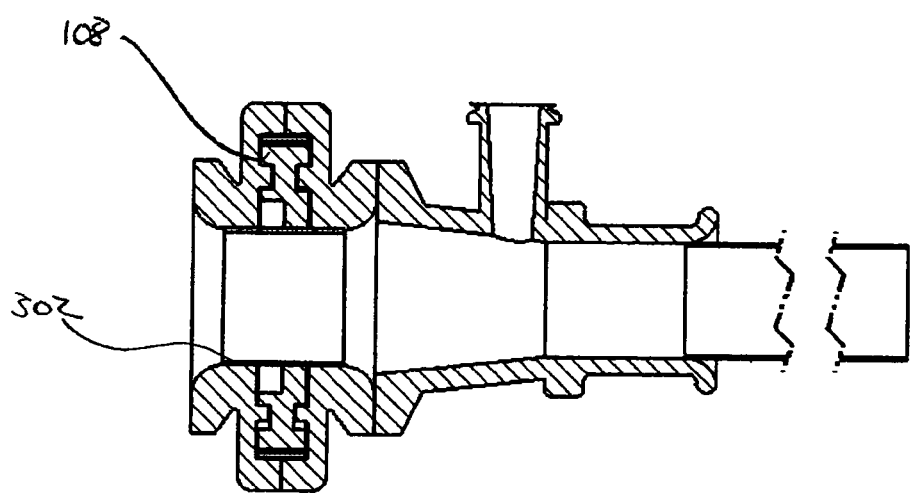

In another embodiment of the invention, one or both of the fixed ends of said valve conduit are independently rotatable. For the purposes of this invention the term "fixed ends" means that rotation member 108 will not rotate the ends of valve conduit (i.e. at the point of attachment of said valve conduit), however one or both of the ends can be rotated by a different mechanism. For example, said ends can be rotated by another rotation member specifically attached to the attachment points of the valve conduit. Thus, in another embodiment of the invention, one or both of the ends can be rotated. This will allows the valve conduit to be open at both ends, as shown in FIG. 3C. In another embodiment, rotating the ends will allow the twists in the valve conduit to be tighter or looser, which will depend on the application and/or the valve conduit material. In another embodiment, when the valve conduit is open at both ends and when the rotatable member is actuated, the valve conduit will twist the valve conduit thus collapsing the valve conduit and closing the valve. In this embodiment, the valve conduit will be either open or closed. In another embodiment, said valve conduit will collapse (i.e. twist shut) on both sides of the rotation member.

A medical device can be inserted into said valve by working said medical device through the valve. One method is by actuating the rotation member opposite directions, thus alternating said valve conduit from open to closed at the ends of said valve conduits. By applying a force that pushes said medical device into the valve, the device will work its way through the valve. Said actions will allow the device to pass through the valve, while maintaining the valve closed. As the device is passed through the valve conduit and the rotation member is actuated, a section of the valve will open, while the other section of the valve collapses around said medical device creating a seal around the device and thus achieving a leak proof seal. In one embodiment, said device is coated with a lubricant to help said devices pass through said valve conduit. In another embodiment, the internal surface of said valve conduit is coated with a lubricant. In another embodiment, both the medical device and valve conduit is coated with a lubricant. In another embodiment, said medical device is selected from the group consisting of catheters, sheaths, and guidewires.

Once said rotation member is actuated, the medical apparatus or actuator may have a means of keeping said rotation member in place to maintain said rotation member in place. In one embodiment, the valve assembly further comprises a latch or means of holding said rotation member in place when said rotation member is actuated. Other means include spring loaded detents, locking screws, locking cams or frictional interference fits. In one embodiment, the ergonomic feature of rotation member 108 can be used in combination with a ratchet spring to hold said rotation member in place. In another embodiment, a rotation member is attached to another member (e.g. a ring) that will directly contact a ratchet spring or other mechanism described above to hold said rotation member in place.

The valve conduit 302 is a conduit for passing medical tools (devices), such as, catheters, sheaths, guidewires, and the like, used in medical procedures. Preferably, the tube is at least a partially compressible conduit that enables a fluid seal around a passed device. The valve conduit may be designed to have any number of different geometrically shaped cross-sections, such as circular, oval, elliptical, diamond, square, polygon, combinations thereof and the like. In addition, the sleeve may narrow along its length, e.g., having a conical shape. For example, a cross-section near the sleeve may be larger than a cross-section at the other end of the tube. Preferably, the tube is designed to have a circular cross-section. In addition, the valve conduit may include localized regions of restricted or enlarged cross-sections.

When utilizing a circular cross-section, the inside diameter of the valve conduit 302 may be in the range from about 1.0 mm to about 30.0 mm or more. In one embodiment, the inside diameter ranges from about 4.0 mm to about 26.0 mm. In another embodiment, the inside diameter ranges from about 4.0 mm to about 8.0 mm. In another embodiment, said valve conduit has a substantial circular cross section. In another embodiment, said valve conduit has a polygon cross-section. In another embodiment, said valve conduit has an inner diameter of at least 3.0 mm.

Depending on the material used, the wall thickness of the valve conduit 302 will depend on the tensile strength of material and ease of twisting said material. A person of skill in the art can readily determine the required wall thickness for an application. In one embodiment, the wall thickness of said flexible sealing tube is from about 0.5 mm to about 2.0 mm.

The length of the valve conduit 302 may vary according to the application. In one embodiment, the length of said valve conduit is from 0.5 cm to about 30.0 cm. In another embodiment, the length of said valve conduit is from about 6.0 cm to about 25.0 cm. In another embodiment, the length of said valve conduit is from about 2.0 cm to about 10.0 cm. A person of skill in the art can readily determine the required length for specific applications.

The valve conduit can be constructed, in whole or in part, utilizing a variety of materials, such as, synthetic materials, natural materials, and combinations thereof. In one embodiment, the flexible sealing tube can be constructed of an elastic polymer such as silicone, polyurethane, latex or the like. Other suitable tube materials include expanded polytetrafluoroethelene (ePTFE), silks, polyester weaves or other medical grade materials. Porous materials can be rendered less pervious to fluids and/or be made more lubricious by filling the tube material voids with an elastomer or other filling agents. The valve conduit can further incorporate reinforcement materials or members such as high strength fibers or ribbons. The valve conduit can also be fabricated from two or more different materials having different mechanical properties such as durometers or degrees of elasticity.

One embodiment of the invention comprises a valve conduit 302 made with at least two types of material. For the purposes of this invention, different types of materials can be made from the same substance(s) but have different properties, for example, different durometer or elasticity. Thus, in one embodiment, the valve conduit has a low durometer inner material combined with a higher durometer outer material. For example said valve conduit can comprise at least two materials having a difference in durometers of about 10%, about 20%, about 30%, about 40%, about 50% or more. The low durometer inner material can more readily conform to an irregular shape and thus facilitate sealing around an inserted device. The higher durometer outer material can support the inner low durometer material and enhance the tear resistance of said conduit. The high durometer material can also increase the compressive force imparted onto the device being inserted into a tube. The difference in durometer can be attributed to a valve conduit made with two different materials or with the same material but is made to have differing durometer, for example by varying the thickness of the material.

The valve conduit can also have a difference in durometers along the length of the tube. For example the tube may have a low durometer on one or both ends, combined with a higher durometer portion in the mid-section of the tube. The valve conduit can also be configured in the opposite form with a higher durometer on an end (or ends) of the valve conduit, with a lower durometer portion in the mid-section of the tube. The difference in durometers can be about 10%, about 20%, about 30%, about 40%, about 50% or more.

The valve conduit 302 can also have a varying wall thickness. For example the valve conduit can have a thick wall at the end (or ends) of the tube combined with a thinner wall in the mid-section of the valve conduit. The valve conduit can also be configured in the opposite form with a thin wall on the end (or ends) with a thicker wall in the mid-section. The tube wall thickness can also be "tapered" with a progressive change in wall thickness along the length of the tube. The difference in wall thickness along the length of a tube can be about 10%, about 20%, about 30%, about 40%, about 50% or more. Combinations of varied durometers, varied materials and various wall thicknesses can be incorporated into the valve conduit. Valve conduits can also have "repeating structures" or repeating segments joined together. For example the properties of a tube can vary along the length of a segment and multiple segments can be joined to form a tube.

The valve conduit 302 can also be "pre-compressed" during assembly of the valve mechanism. For example a conduit having a free, unconstrained length of about 4 cm can have a pre-compressed length of about 3 cm after being assembled into a valve mechanism. Pre-compressing the conduit reduces the conduit's wall tension as the conduit is twisted. Less tension in the conduit wall increases the conformability of the conduit, resulting in enhanced sealing around a device. The difference between a free unconstrained conduit length and a pre-compressed conduit length can be about 3%, about 5%, about 7%, about 10%, about 15%, about 20%, about 25%, about 30% or more.

To aid in the insertion of a medical device into the valve conduit 302, a lubricious material, coating or liner may be incorporated onto the inner diameter of the tube as commonly known in the art. In addition anti-microbial and/or therapeutic agents can be applied to the valve conduit.

In another embodiment, said hemostatic valve comprises at least one additional sealing mechanism. In one embodiment, said at least one additional sealing mechanism is selected from the group consisting of an elastic diaphragm, a cap, a twistable conduit, brushes, and an inflatable valve or a combination thereof. In another embodiment, said at least one additional sealing mechanisms comprises at least one cap. In another embodiment, said at least one cap has more than one opening to let medical devices pass through. For example, said cap can accommodate a catheter and a guidewire through different openings (see e.g. U.S. Pat. Nos. 5,006,113, 6,416,499, 6,086,570, 6,610,031 and 7,172,580 which are incorporated by reference herein). Said opening can be customized for a particular device and use.

Another embodiment of the invention comprises a hemostatic valve comprising a twistable valve conduit with first and second fixed ends and a rotatable member positioned between the first and second ends. In one embodiment, said valve is never fully opened. In another embodiment, said rotatable member is directly attached to the valve conduit. In another embodiment, said rotatable member is indirectly attached to the valve conduit, as discussed above.

In another embodiment of the invention, said hemostatic valve further comprises a latch or means of holding said rotatable member in place when said rotatable member is actuated, as discussed above. In another embodiment, one or both of the fixed ends are independently rotatable. In another embodiment, said hemostatic valve is a component of a vascular introducer sheath. In another embodiment, said twistable valve conduit has a substantial circular cross section. In another embodiment, said twistable valve conduit has a polygon cross-section. In another embodiment, said twistable valve conduit has an inner diameter of at least 3 mm. In another embodiment, said twistable valve conduit comprises a material selected from the group consisting of expanded polytetrafluoroethelene (ePTFE), silks, polyester weaves and porous filled materials. In another embodiment, said twistable valve conduit comprises two or more different materials having different mechanical properties such as durometers or degrees of elasticity.

In another embodiment, said hemostatic valve further comprises at least one additional sealing mechanism. In another embodiment, said at least one additional sealing mechanism is selected from the group consisting of an elastic diaphragm, a cap, a twistable conduit, brushes, and an inflatable valve or a combination thereof. In another embodiment, said at least one additional sealing mechanism comprises at least one cap. In another embodiment, said at least one cap has more than one opening to let medical devices pass through (as described above). In another embodiment, said twistable valve conduit has a length in the range from about 6 mm to about 25 mm. In another embodiment, a region of said twistable valve conduit collapses around at least one medical device inserted into said conduit when said rotatable member is actuated. In another embodiment, said medical device is selected from the group consisting of catheters, sheaths, and guidewires.

Another embodiment of the invention comprises a medical apparatus, comprising: a housing, a sheath; and a valve; wherein said valve comprises a twistable valve conduit with first and second fixed ends and a rotatable member positioned between the first and second ends. In another embodiment, said valve is never fully opened. In another embodiment, said medical apparatus prevents the loss of bodily fluids. By preventing the loss of bodily fluids it is meant that no or an insignificant amount of bodily fluids will leak from said valve of the invention. In another embodiment, said medical apparatus is a vascular introducer sheath. In another embodiment, said rotatable member is directly attached to said twistable valve conduit. In another embodiment, said rotatable member is indirectly attached to said twistable valve conduit. In another embodiment, one of the fixed ends is independently rotatable, as described above. In another embodiment, said medical apparatus further comprises a latch or means of holding said rotatable member in place when said rotatable member is actuated. In another embodiment, said twistable valve conduit has a substantial circular cross section. In another embodiment, said twistable valve conduit has a polygon cross-section. In another embodiment, said twistable valve conduit has an inner diameter of at least 3 mm. In another embodiment, said twistable valve conduit comprises a material selected from the group consisting of expanded polytetrafluoroethelene (ePTFE), silks, polyester weaves and porous filled materials. In another embodiment, said twistable valve conduit comprises two or more different materials having different mechanical properties such as durometers or degrees of elasticity 9 as described above). In another embodiment, said medical apparatus further comprising at least one additional sealing mechanism. In another embodiment, said at least one additional sealing mechanism is selected from the group consisting of an elastic diaphragm, a cap, a twistable conduit, brushes, and an inflatable valve or a combination thereof. In another embodiment, said at least one additional sealing mechanisms comprises at least one cap. In another embodiment, said at least one cap has more than one opening to let medical devices pass through (as described above). In another embodiment, said twistable valve conduit has a length in the range from about 6 mm to about 25 mm. In another embodiment, a region of said twistable valve conduit collapses around at least one medical device inserted into said conduit when said rotatable member is actuated. In another embodiment, said medical device is selected from the group consisting of catheters, sheaths, and guidewires.

This invention is further illustrated by the following examples which should not be construed as limiting. The contents of all the Figures are incorporated herein by reference.

EXAMPLES

Example 1

Materials

A hemostatic valve assembly similar to FIG. 1 was manufactured using the following components and assembly process:

The housing and the rotation member as shown in the figures were originally fabricated on a lathe and vertical mill out of polycarbonate and later by were fabricated by Proto-Cam (Northampton, Pa.) using stereolithography (SLA) material designated as Accura® 60. Other parts were also fabricated using the SLA process. These parts include the housing (including the flush port) and rotation member. As stated above the flush port is an optional add-on part. The ratchet spring was hand formed out of spring steel. See FIG. 4 for an exploded view of this assembly and Table 1 for the label numbers and the name and quantity of the parts.

TABLE 1

Figure 4:
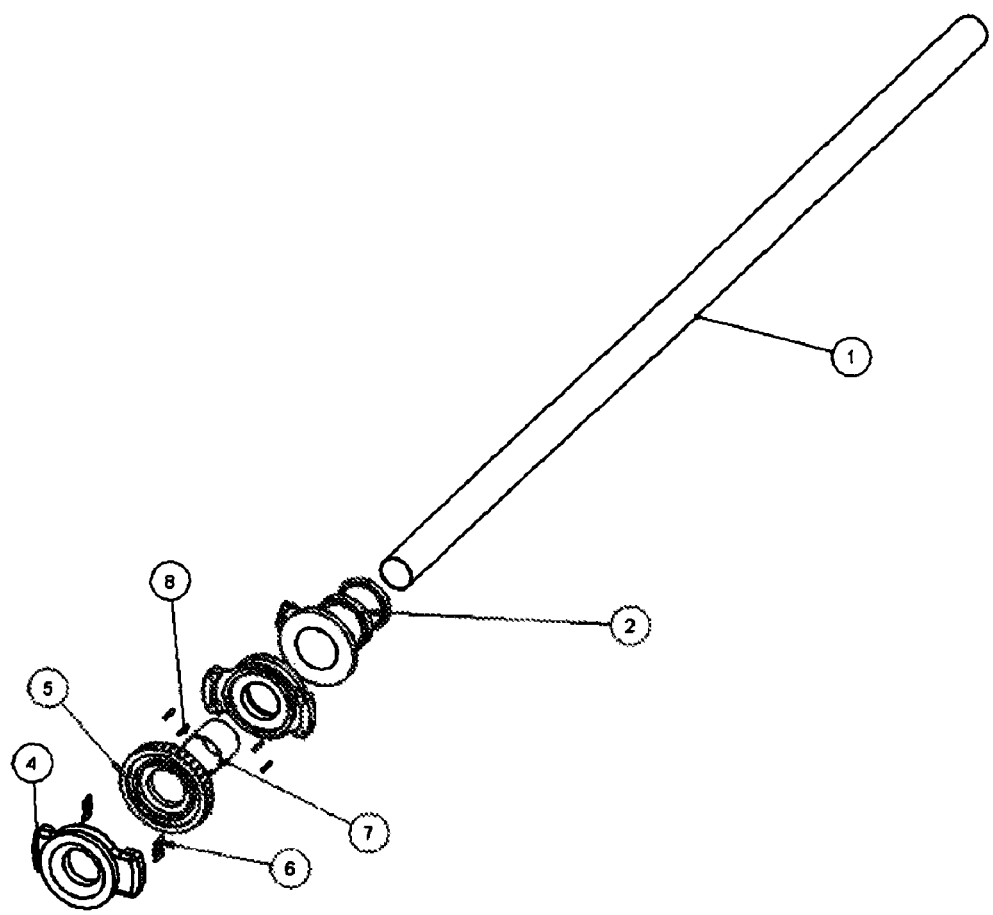
FIG. 4 depicts an exploded view of the introducer sheath.

Part Label For FIG. 4

| Label Number | Part | Quantity |
|---|---|---|
| 1 | Sheath | 1 |
| 2 | Housing (Flush port) | 1 |
| 4 | Housing | 2 |
| 5 | Rotation member | 1 |
| 6 | Ratchet Spring | 2 |
| 7 | Valve Conduit | 1 |
| 8 | Dowel Pins | 4 |

Other materials required for the assembly of the valve conduit were purchased. An elastomeric tube (used for the twist sealing component) having a outer diameter of about 0.4" (10 mm), a wall thickness of about 0.03" (0.8 mm) and a length of about 1.0" (25 mm) was procured from Specialty Silicone Fabricators (Paso Robles, Calif.). This tube was formed of an elastomeric silicone having a duromteter of about 30 A. Four dowel pins (FIG. 4) were purchased to be pressed into the holes on the housing to hold the valve together. These dowel pins were made of stainless steel with lengths of about 0.1875" (4.76 mm), diameters of about 0.03125" (0.794 mm), and were procured from McMaster Carr (Elmhurst, Ill.). Loctite 495R (super glue) and a sheath was supplied by in-house stock.

Example 2

Assembly of the Introducer Sheath

The introducer sheath was then assembled using the components described above and as shown in FIG. 4. The longitudinal center of the silicone tube (valve conduit) was glued into the inner diameter of the rotation member. Then the four dowel pins were pressed into one side of the housing. The ratchet springs were then inserted into pockets on the same face of the housing as the dowel pins. Following this step the silicone tube was slipped through both sides of the housing. With the silicone tube through both housings, glue was applied to one of the housing faces; the dowel pins were aligned and pressed into the complimentary holes until the housing faces mated. The ends of the silicone tube were then constrained on the outer housing faces by stretching it over the outside diameter of each outer housing face.

Example 3

Leak Test of the Introducer Sheath

The assembled introducer sheath was then tested. A pump that used air to pressurize the water at a regulated psig (around 6 psi) with a heater cartridge in the holding/pressure vessel that heater the water to about 37° C. The sheath attached to the hemovalve was inserted into a quick connect airline fitting on the pump. To test the valve, different medical devices were inserted in the valve and the rotation member was turned so that the valve conduit collapses around the device and to create a seal. The medical devices used for this experiment are: a guide wire (GW), two guidewires (2GW), a catheter alone or a catheter with a guidewire (GW & catheter). The tests were conducted by pumping heated water (37° C.) into the sheath for 30 seconds at a pressure of 6.2 psi. The average artery has a pressure of about 2 psi. The volume of water the leaked through the valve was captured and measured using a graduated cylinder. After each test the volume reading was recorded. Leakage data for this valve's performance is found on the Table 2 below.

TABLE 2

| Leak Test Data | | | | |
|---|---|---|---|---|
| No devices | 1 GW | 2 GW | 1 Catheter | 1 GW & 1 catheter |
| <1 ml | 2 ml | 5 ml | 4 ml | 45 ml |

These data show that that there is very little leakage from the valve at high pressures. Thus, this valve is an effective hemovalve.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A hemostatic valve comprising:
   twistable valve conduit with firs and second fixed ends, said value conduit having first and second regions, said regions each having an open and closed configuration, wherein said valve conduit is open in one region and closed in the other region; and
   a rotation member attached to a center portion of said conduit, between said first and second regions of said conduit, wherein when said rotation member is actuated, said actuation alternates each region between open and closed configurations.

2. The hemostatic valve of claim 1, wherein said valve conduit is never fully opened.

3. The hemostatic valve of claim 1, wherein said rotatable member is directly attached to the valve conduit.

4. The hemostatic valve of claim 1, wherein said rotatable member is indirectly attached to the valve conduit.

5. The hemostatic valve of claim 1, wherein said hemostatic valve further comprises a latch or means of holding said rotation member in place when said rotation member is actuated.

6. The hemostatic valve of claim 1, wherein said hemostatic valve is a component of a vascular introducer sheath.

7. The hemostatic valve of claim 1, wherein said valve conduit has a substantial circular cross section.

8. The hemostatic valve of claim 1, wherein said valve conduit has a polygon cross-section.

9. The hemostatic valve of claim 1, wherein said valve conduit has an inner diameter of at least 3 mm.

10. The hemostatic valve of claim 1, wherein said valve conduit comprises a material selected from the group consisting of expanded polytetrafluoroethelene (ePTFE), silks, polyester weaves and porous filled materials.

11. The hemostatic valve of claim 1, further comprising at least one additional sealing mechanism.

12. The hemostatic valve of claim 11, wherein said at least one additional sealing mechanism is selected from the group consisting of an elastic diaphragm, a cap, a twistable conduit, brushes, and an inflatable valve or a combination thereof.

13. The hemostatic valve of claim 12, wherein said at least one additional sealing mechanisms comprises at least one cap.

14. The hemostatic valve of claim 13, wherein said at least one cap has more than one opening to let medical devices pass through.

15. The hemostatic valve of claim 1, wherein said twistable valve conduit has a length in the range from about 6 mm to about 25 mm.

16. The hemostatic valve of claim 1, wherein at least one region of said valve conduit collapses around at least one medical device inserted into said conduit when said rotation member is actuated.

17. The hemostatic valve of claim 16, wherein said medical device is selected from the group consisting of catheters, sheaths, and guidewires.

18. A hemostatic valve comprising: a twistable valve conduit with first and second fixed ends and a rotatable member coupled to a center of said conduit between said first and second ends of said conduit.

19. The hemostatic valve of claim 18, wherein said valve is never fully opened.

20. The hemostatic valve of claim 18, wherein said rotatable member is directly attached to the valve conduit.

21. The hemostatic valve of claim 18, wherein said rotatable member is indirectly attached to the valve conduit.

22. The hemostatic valve of claim 18, wherein one of the fixed ends is independently rotatable.

23. The hemostatic valve of claim 18, wherein said hemostatic valve further comprises a latch or means of holding said rotatable member in place when said rotatable member is actuated.

24. The hemostatic valve of claim 18, wherein said hemostatic valve is a component of a vascular introducer sheath.

25. The hemostatic valve of claim 18, wherein said twistable valve conduit has a substantial circular cross section.

26. The hemostatic valve of claim 18, wherein said twistable valve conduit has a polygon cross-section.

27. The hemostatic valve of claim 20, wherein said twistable valve conduit has an inner diameter of at least 3 mm.

28. The hemostatic valve of claim 18, wherein said twistable valve conduit comprises a material selected from the group consisting of expanded polytetrafluoroethelene (ePTFE), silks, polyester weaves and porous filled materials.

29. The hemostatic valve of claim 18, further comprising at least one additional sealing mechanism.

30. The hemostatic valve of claim 29, wherein said at least one additional sealing mechanism is selected from the group consisting of an elastic diaphragm, a cap, a twistable conduit, brushes, and an inflatable valve or a combination thereof.

31. The hemostatic valve of claim 30, wherein said at least one additional sealing mechanism comprises at least one cap.

32. The hemostatic valve of claim 31, wherein said at least one cap has more than one opening to let medical devices pass through.

33. The hemostatic valve of claim 18, wherein said twistable valve conduit has a length in the range from about 6 mm to about 25 mm.

34. The hemostatic valve of claim 18, wherein a region of said twistable valve conduit collapses around at least one medical device inserted into said conduit when said rotatable member is actuated.

35. The hemostatic valve of claim 34, wherein said medical device is selected from the group consisting of catheters, sheaths, and guidewires.

36. A medical apparatus, comprising:
   a housing;
   a sheath; and
   a valve;
   wherein said valve comprises a twistable valve conduit with first and second fixed ends and a rotatable member coupled to a center of said conduit between said first and second ends of said conduit.

37. The medical apparatus of claim 36, wherein said valve is never fully opened.

38. The medical apparatus of claim 36, wherein said medical apparatus prevents the loss of bodily fluids.

39. The medical apparatus of claim 38, wherein said medical apparatus is a vascular introducer sheath.

40. The medical apparatus of claim 36, wherein said rotatable member is directly attached to said twistable valve conduit.

41. The medical apparatus of claim 36, wherein said rotatable member is indirectly attached to said twistable valve conduit.

42. The medical apparatus of claim 36, wherein one of the fixed ends is independently rotatable.

43. The medical apparatus of claim 36, wherein said medical apparatus further comprises a latch or means of holding said rotatable member in place when said rotatable member is actuated.

44. The medical apparatus of claim 36, wherein said twistable valve conduit has a substantial circular cross section.

45. The medical apparatus of claim 36, wherein said twistable valve conduit has a polygon cross-section.

46. The medical apparatus of claim 36, wherein said twistable valve conduit has an inner diameter of at least 3 mm.

47. The medical apparatus of claim 36, wherein said twistable valve conduit comprises a material selected from the group consisting of expanded polytetrafluoroethelene (ePTFE), silks, polyester weaves and porous filled materials.

48. The medical apparatus of claim 36, further comprising at least one additional sealing mechanism.

49. The medical apparatus of claim 48, wherein said at least one additional sealing mechanism is selected from the group consisting of an elastic diaphragm, a cap, a twistable conduit, brushes, and an inflatable valve or a combination thereof.

50. The medical apparatus of claim 49, wherein said at least one additional sealing mechanisms comprises at least one cap.

51. The medical apparatus of claim 50, wherein said at least one cap has more than one opening to let medical devices pass through.

52. The medical apparatus of claim 36, wherein said twistable valve conduit has a length in the range from about 6 mm to about 25 mm.

53. The medical apparatus of claim 36, wherein a region of said twistable valve conduit collapses around at least one medical device inserted into said conduit when said rotatable member is actuated.

54. The medical apparatus of claim 53, wherein said medical device is selected from the group consisting of catheters, sheaths, and guidewires.

* * * * *